(12) United States Patent
Martinez

(10) Patent No.: US 10,130,441 B2
(45) Date of Patent: Nov. 20, 2018

(54) CLIP-ON AFFIXABLE LIGHT SOURCE

(71) Applicant: Millie Martinez, Placentia, CA (US)

(72) Inventor: Millie Martinez, Placentia, CA (US)

( * ) Notice: Subject to any disclaimer, the term of this patent is extended or adjusted under 35 U.S.C. 154(b) by 0 days.

(21) Appl. No.: 14/707,702

(22) Filed: May 8, 2015

(65) Prior Publication Data

US 2016/0327253 A1 Nov. 10, 2016

(51) Int. Cl.
*F21V 21/08* (2006.01)
*F21V 21/088* (2006.01)
*A61B 90/35* (2016.01)
*A61B 90/30* (2016.01)

(52) U.S. Cl.
CPC .............. *A61B 90/35* (2016.02); *A61B 90/30* (2016.02); *A61B 2090/309* (2016.02)

(58) Field of Classification Search
CPC ...................................................... F21V 21/088
USPC ............................................................. 362/396
See application file for complete search history.

(56) References Cited

U.S. PATENT DOCUMENTS

| 7,497,584 B1* | 3/2009 | Quittner ............... F21L 4/045 362/103 |
| 2007/0081358 A1* | 4/2007 | Shea ........................ F21L 4/04 362/572 |
| 2009/0059607 A1* | 3/2009 | Yoon ....................... F21L 4/02 362/396 |

* cited by examiner

*Primary Examiner* — William Carter
(74) *Attorney, Agent, or Firm* — Global Intellectual Property Agency, LLC; Daniel Boudwin

(57) ABSTRACT

A clip-on light source is provided that is suited for use with medical instruments. The device comprises a light source housing that is rotatably affixed to a spring biased clip. The clip includes an upper clip member and a lower clip member that are hinged and spring biased together. The upper clip member is rotatably affixed to the lower surface of the housing such that the housing can rotate relative to the clip once the clip is affixed to a support surface. The housing comprises a frontal portion, an upper portion, and an interior volume, whereby the interior volume supports a circuit board, a battery power supply, and the light source. The light source projects through an upper surface projection along the housing, whereby the light is directed along the upper surface of the housing and towards the frontal portion.

5 Claims, 2 Drawing Sheets

CLIP-ON AFFIXABLE LIGHT SOURCE

BACKGROUND OF THE INVENTION

Field of the Invention

The present invention relates to medical equipment light sources. More specifically, the present invention relates to a compact and attachable light source that is affixable to a medical instrument during a procedure that projects light into a body cavity or against a work surface.

Many medical procedures involve examination of internal body cavities or areas of low light. These include procedures into which tools are used to expand a body opening for access. Common appliances include speculums, spreading tools, and others. The present invention relates to an independent light source that can be used when inspecting and operating in various cavities and across different fields of medical and dental practice.

A spreading instrument is a medical device that allows a physician to visually inspect an internal body cavity by separating an opening to allow visual access thereinto. A speculum is a common example, which comprises a hand-held device having a plurality of 'blades' to separate an opening to a body cavity and allow direct vision between the blades and into the cavity of interest. Examinations of this type can be facilitated in conjunction with a light source, preferably a fiber optic light that can be placed into the body cavity for direct illumination. While such light sources provide a means to illuminate the cavity, these light sources generally require the examiner to hold both the speculum and the light source simultaneously, while at the same time conducting the examination. This can be a cumbersome activity given the needs of the examiner to visually expect and then conduct any medical procedures necessary during the examination.

The present invention is provided to improve handling and control of the medical tool while offering a light source for improved clarity of the area being inspected or operated upon. The present invention is one that is designed to secure to the medical instrument to free the hands of the operator, while also offering a small device that does not interfere with the tool or the procedure. Finally, the present invention is one that can be readily removed from the medical instrument, and either replaced with another example or cleaned prior to reuse with another patient. In this way, the present invention provides convenience and a sterile application of light for different procedures.

The present invention specifically comprises a light source disposed within a housing that comprises a rotatable clip, whereby the light source is disposed within the housing and the housing is clipped to a medical instrument of choice for a given procedure. A contemplated function of the light source device is to provide illumination while operating a medical instrument; however, nothing in the background of the invention section or in the detail description should be construed as limiting the present invention to use in such environments. The present invention provides a light source that includes a spring biased clip, whereby the light source is disposed within a housing that is rotatable relative to the clip. The device may be deployed in any manner and in a plurality of environments where a small, clip-on light source is desirable. The device is an inexpensive, replaceable, and readily attachable light source suitable for diverse usage.

SUMMARY OF THE INVENTION

The following summary is intended solely for the benefit of the reader and is not intended to be limiting in any way.

The present invention provides a new clip-on light source that can be utilized for providing convenience for the user when illuminating an area adjacent to a tool or a support, whereby the light source can support itself without user interaction.

It is therefore an object of the present invention to provide a new and improved clip-on illumination device that has all of the advantages of the prior art and none of the disadvantages.

It is another object of the present invention to provide a clip-on illumination device that comprises a high intensity light source that can be affixed to an instrument, tool, or to a work surface for illuminating an area without requiring the user to handle the illumination device.

Another object of the present invention is to provide a clip-on illumination device that includes a spring-biased clip and a light source housing that are in rotatable relation to one another such that the light source direction can be altered after the clip has been affixed to a support surface.

Yet another object of the present invention is to provide a clip-on illumination device that comprises a small, battery powered assembly that does not consume considerable volume and is well suited for attachment to medical instruments during a procedure.

Another object of the present invention is to provide a clip-on illumination device that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
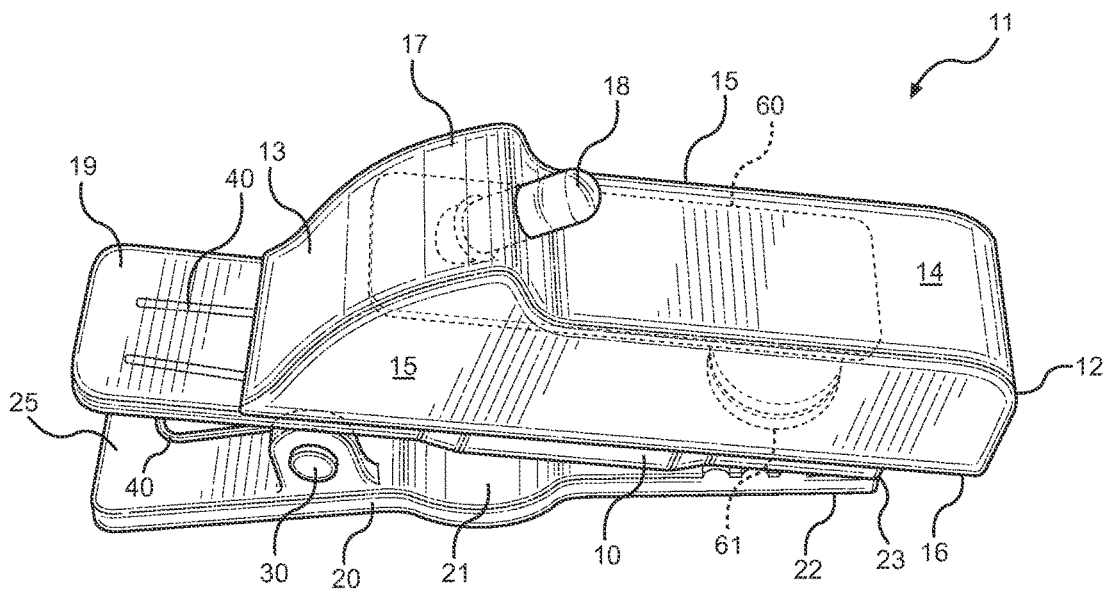
FIG. 1 shows an overhead perspective view of the clip-on illumination device of the present invention.

Reference is made herein to the attached drawings. Like reference numerals are used throughout the drawings to depict like or similar elements of the clip-on illumination device of the present invention. For the purposes of presenting a brief and clear description of the present invention, the preferred embodiment will be discussed as used for illuminating an area adjacent to a tool, instrument, or surface, whereby the light source can be clipped thereto and used to illuminate an area without the user handling the device. The figures are intended for representative purposes only and should not be considered to be limiting in any respect.

Figure 2:
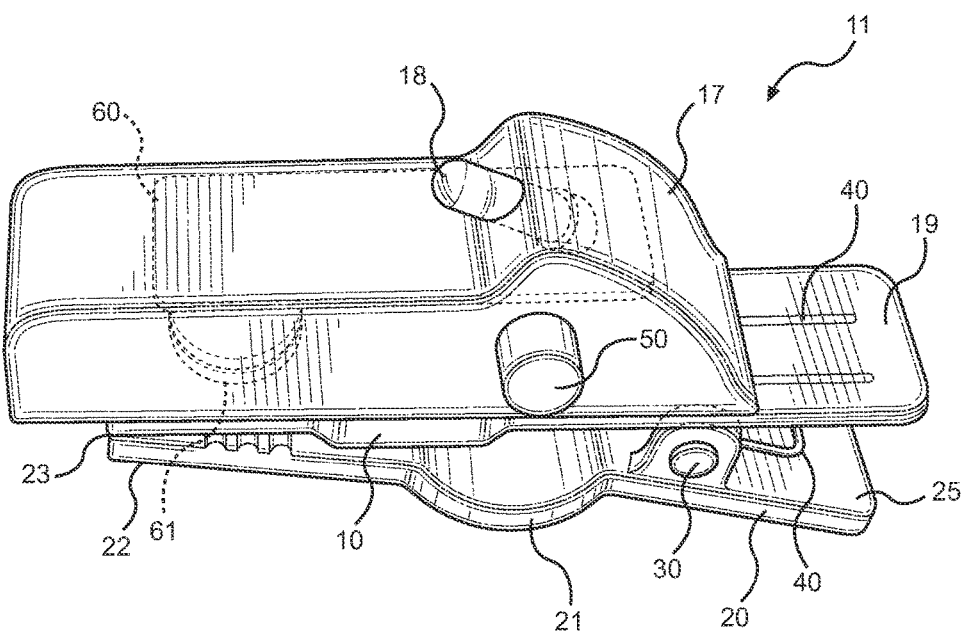
FIG. 2 shows another overhead perspective view of the clip-on illumination device of the present invention.

Referring now to FIGS. 1 and 2, there are shown a pair of perspective views of the illumination device of the present invention. The illumination device is a clip-on light source that is designed to provide concentrated, high intensity illumination in an area adjacent to a structure, whereby the device secures to the structure and can be supported thereby without user interaction. The device is well suited for attachment to tools, medical instruments, on clothing, or for providing light adjacent to any exposed surface upon which the device can be clamped thereto.

The device comprises a light source housing 11 that comprises a front portion 12, a rear portion 13, an interior volume, an upper surface 14, and a lower surface 16. The housing 11 supports a light source 18 therein, which is preferably a light emitting diode powered by a battery power supply 61 and controlled via an electric circuit 60. The light source 18 projects from the housing and towards the front portion 12, projecting light from the front portion 12 and onto a work surface or into a cavity.

In a preferred configuration, the upper surface 14 of the housing 11, along the rear portion 13 thereof, includes a light source projection 17 extending therefrom. The light source projection 17 is a protruding portion along the upper surface 14 of the housing that shrouds the light source 18 and directs the light sources towards the front portion 12 of the housing. The light source 18 is preferably angled forward and slightly upward from the housing, projecting light forward and away from the lower surface 16 of the housing. The light source 18 itself may be embedded completely within the light source projection 17, or alternatively a portion thereof may be exposed from the light source projection 17 as provided in the figures. When the light source 18 is exposed from the light source projection 17, the light source may further include a lens thereover or a cap, which cover the light source 18 and furthermore prevents fluid from entering the housing interior.

The electric circuit 60 within the housing controls the flow of current from the battery power source 61 to the light source 18, and furthermore receives signals from an activation switch 50 along the housing exterior surface. The activation switch 50 controls the operation of the light source 18, whereby the user can operably energize and/or control the intensity of the light source 18. In one embodiment, the switch 50 provides a simple on/off switch that can energize or cease operation of the light source 18. In another embodiment, the switch 50 further comprises a rotatable dimmer switch that can control the intensity of light being produced by the light source 18. Finally, the switch may form a multi-state switch, providing different set intensities from the light source 18 (e.g. a three-position switch or equivalent). In any embodiment, the switch 50 controls the flow of power from the batteries 61 and to the light source 18, allowing the user to control operation of the light. The switch may be disposed on any one of the exterior surfaces of the housing 11.

The housing 11 is one that can be supported by a surface and without the direct interaction of the user. This is accomplished using a spring biased clip assembly along the lower surface 16 of the housing 11. The clip comprises an upper clip member 10 and a lower clip member 20, which are hingedly attached and spring biased together. A torsion spring 40 is provided between the clip members, whereby the spring 40 is connected to a pin joint 30 between the two and is used to bias the clip members. The spring biases the front portions 23, 22 of the upper and lower clip members together, and biases the rear portions 19, 25 of the upper and lower clip members apart. Therefore, the rear portions 19, 25 are separated under normal conditions and can be pinched together by the user to separate the front portions 22, 23 of the upper and lower clip members. A support is placed between the front portions 22, 23 and the rear portions 19, 25 are released, thereby causing the front portions 22, 23 to clamp the support therebetween using the force of the spring 40 to bias the two together.

The upper clip member 10 is affixed to the lower surface 16 of the housing 11, and is preferably connected using a rotational joint. The upper clip member 10 can therefor pivot relative to the housing 11 such that the housing 11 and the light source 18 can be directed towards a given area after the clip assembly has been secured to a support structure. This allows a user to direct light where required without removing or adjusting the clip position against a tool, instrument, or other support. The lower surface 16 of the housing 11 and the upper clip member 10 are preferably parallel to one another, whereby the rotational joint connecting the two is preferably a revolute joint that allows the housing 11 to rotate in a plane that is parallel to the lower surface 16 of the housing 11 and parallel to the upper surface of the upper clip member 10. This is best represented in drawing FIG. 4.

Figure 3:
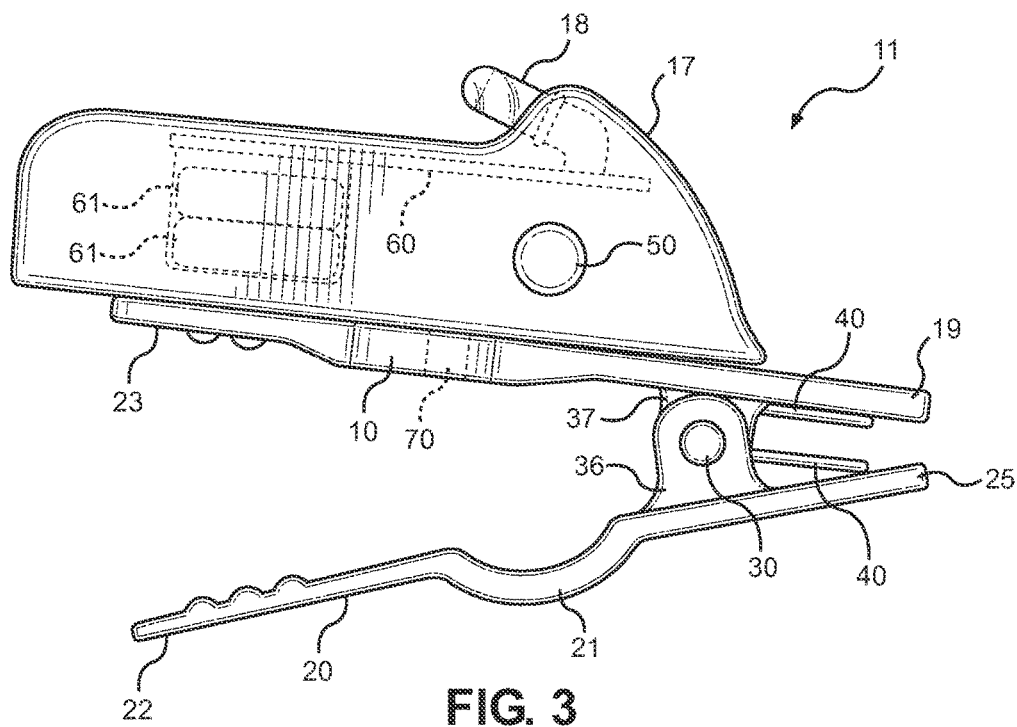
FIG. 3 shows a side view of the clip-on illumination device of the present invention.
Figure 4:
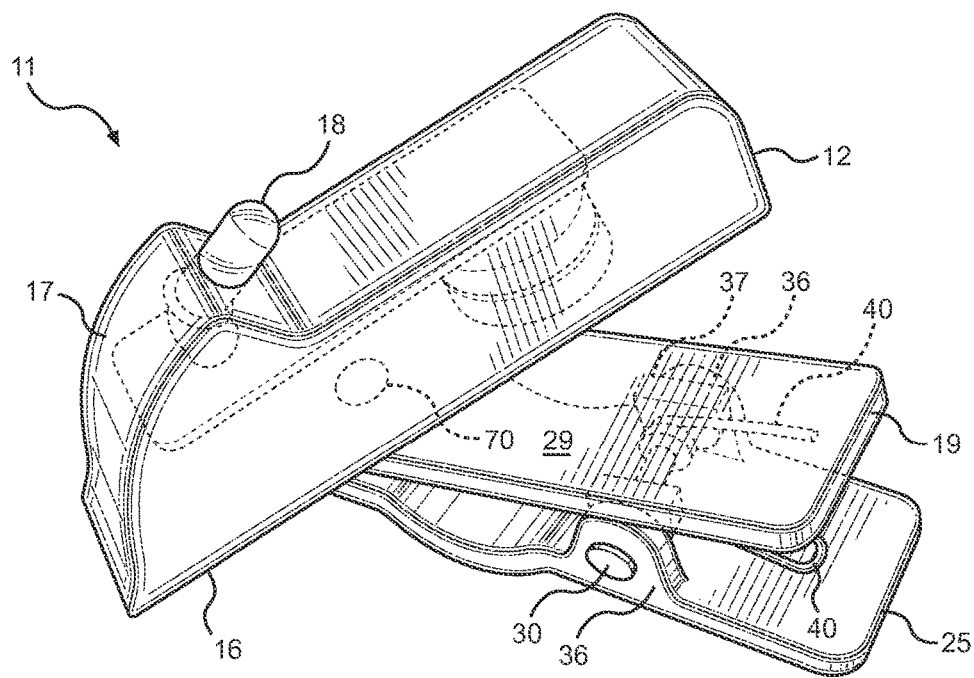
FIG. 4 shows a view of the clip-on illumination device in which the light source housing is rotated relative to the clip assembly.

Referring now to FIGS. 3 and 4, there is a shown a side view and a perspective view of the illumination device of the present invention. FIG. 3 shows the illumination device in a condition in which the clip assembly is in an open position and the front portions 23, 22 of the clip members 10, 20 are separated, and the rear portions 19, 40 of the clip members 10, 20 are pressed together. In this position, the spring 40 is being compressed and a surface of an instrument, tool, or support is placed between the front portions 23, 22. FIG. 4 shows an overhead perspective view that illustrates the adjustability of the housing 11 relative to the clip assembly. The housing 11 can rotate relative to the upper clip member 10 to direct the light source 18 in a desired direction after the clip assembly has been connected to a support. This allows adjustment of the light source 18 after the device has been connected to a tool, instrument, or support. Between the housing lower surface 16 and the upper clip member 10 is a revolute joint 70, which allows the housing 11 to rotate relative to the clip assembly.

Between the upper 10 and lower 20 clip members is a pin joint 30 and the spring 40. Each of the clip members has a pair of clevises 36, 37, which overlap on another to form an elongated opening that can support a pin therethrough. This allows the clip members to rotate about a single axial line (i.e. through the pin 30 axial direction). The spring 40 is coiled around the pin 30 and includes spring arms, which extending towards the rear portions 19, 25 of the clip members, biasing the same apart from one another.

Within the housing interior is the battery power source 61, the electric circuit 60, and the light source 18. The power source 61 may comprise one or more batteries 61, which supply power to the light source 18 via the circuit 60 and the activation switch 50. The electric circuit 60 is preferably a printed circuit board (PCB) that connects the batteries 61, the activation switch 50, and the light source 18. The PCB controls operation of the light source, regulating power delivery and receiving input from the activation switch 50. The light source 18 is preferably a light emitting diode (LED) powered by the batteries 61 and controlled by the PCB 60. Overall, the internal components of the housing are shrouded from the exterior environment, whereby the components can operate in damp or moist environments. Furthermore, the components of the device, including electrical and structural components, are suitable for sterile operation. Moreover, the components may be constructed of inexpensive materials to accommodate ready replacement and/or disposal after use in medical procedures.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A clip-on affixable light source, comprising:
an enclosed and elongated housing having a front portion, a rear portion, an interior volume, an upper surface, and a lower surface;
the rear portion comprising a light source projection extending from the upper surface of the housing;
a light source disposed within the light source projection, the light source extending upwardly out of the housing, positioned over the front portion of the housing, and directed towards the front portion of the housing;
a battery power supply, a circuit, and an activation switch electrically coupled to the light source;
a clip attached to the lower surface of the housing that is adapted to pinch a support and connect the housing thereto;
wherein the front portion of the housing is rotatably attached to the clip, the housing configured to rotate in a parallel orientation relative to the clip;
wherein the clip further comprises an upper clip member and a lower clip member that are hingedly attached and spring biased together, the lower clip member comprising an arcuate protrusion forming a channel extending transverse therefrom, the protrusion oriented in a direction opposing the upper clip member and defining a recession configured to receive an object therein;
wherein the upper clip member and the lower clip member each further comprise a pair of devices that are pinned together to form a hinge joint;
the upper clip member having a front portion and a rear portion;
the lower clip member having a front portion and a rear portion;
the front portions of the upper clip member and the lower clip members being biased together by a torsion spring about the hinge joint;
the rear portions of the upper clip member and the lower clip members being exposed from the rear portion of the housing to permit a user to pinch the rear portions together to separate the front portions of the upper clip member and the lower clip members;
wherein the housing is configured such that the front portion of the housing extends forward past the front portion of the upper clip member and the front portion of the lower clip member when the housing is oriented in a first position, wherein the housing is parallel to each of the upper clip member and the lower clip member when the housing is oriented in the first position, wherein the rear portion of the upper clip member and the rear portion of the lower clip member each extend rearward past the rear portion of the housing when the housing is oriented in the first position.

2. The light source of claim 1, further comprising a dimmer control for the light source.

3. The light source of claim 1, wherein the activation switch further comprises a three-position switch.

4. The light source of claim 1, wherein the light source further comprises a light emitting diode.

5. The light source of claim 1, wherein the light source further comprises a light bulb.

* * * * *